(12) United States Patent
Hafey

(10) Patent No.: US 9,808,431 B2
(45) Date of Patent: *Nov. 7, 2017

(54) IMMEDIATE RELEASE ORAL GUAIFENESIN SOLUTION

(71) Applicant: SOVEREIGN PHARMACEUTICALS, LLC, Fort Worth, TX (US)

(72) Inventor: Paul Hafey, Keller, TX (US)

(73) Assignee: Sovereign Pharmaceuticals, LLC, Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/401,318

(22) Filed: Jan. 9, 2017

(65) Prior Publication Data

US 2017/0135965 A1    May 18, 2017

Related U.S. Application Data

(63) Continuation of application No. 14/940,455, filed on Nov. 13, 2015, now Pat. No. 9,549,907.

(51) Int. Cl.
*A61K 31/09* (2006.01)
*A61K 9/00* (2006.01)
*A61K 45/06* (2006.01)
*A61K 47/10* (2017.01)
*A61K 31/137* (2006.01)

(52) U.S. Cl.
CPC ........... *A61K 31/09* (2013.01); *A61K 9/0053* (2013.01); *A61K 31/137* (2013.01); *A61K 45/06* (2013.01); *A61K 47/10* (2013.01)

(58) Field of Classification Search
USPC ....................................................... 514/282
See application file for complete search history.

(56) References Cited

U.S. PATENT DOCUMENTS

| 9,549,907 B1 * | 1/2017 | Hafey ............... A61K 31/09 |
| 2003/0113377 A1 | 6/2003 | Dobrozsi |
| 2007/0160689 A1 | 7/2007 | Giordano |
| 2014/0243364 A1 | 8/2014 | Agisim |
| 2014/0275151 A1 | 9/2014 | Bharati |

* cited by examiner

*Primary Examiner* — Rei Tsang Shiao
(74) *Attorney, Agent, or Firm* — Abel Law Group, LLP

(57) ABSTRACT

Disclosed is an immediate release solution for oral administration of guaifenesin and at least one additional drug. In addition to water the solution comprises as solvents propylene glycol and glycerol in a concentration which significantly increases the bioavailability of guaifenesin in the human body.

20 Claims, No Drawings

IMMEDIATE RELEASE ORAL GUAIFENESIN SOLUTION

CROSS-REFERENCE TO RELATED APPLICATIONS

The present application is a continuation of application Ser. No. 14/940,455, filed Nov. 13, 2015, the entire disclosure of which is expressly incorporated by reference herein.

BACKGROUND OF THE INVENTION

1. Field of the Invention

The present invention relates to an immediate release guaifensin solution for oral administration and in particular, a guaifenesin solution which in addition to water, contains concentrations of propylene glycol and glycerol which significantly improve the bioavailability of the guaifenesin in the human body.

2. Discussion of Background Information

Orally administered pharmaceutical compositions are provided to patients in many dosage forms, including solid forms such as capsules, caplets or tablets and liquid forms such as solutions and suspensions. Due to these issues with swallowing, oral solutions are preferred for many pharmaceutical products, especially those products that will be used in children and geriatric patients. One such category is cough and cold products. As with all other dosage forms, it is desirable for oral dosage forms to provide a degree of bioavailability of the drug(s) to be administered that is as high as possible. It has now unexpectedly been found that by including two organic solvents, i.e., propylene glycol and glycerol, in an aqueous guaifenesin solution for oral administration the bioavailability of the guaifenesin can be improved significantly, as evidenced by, for example, a significantly increased $C_{max}$ (maximum plasma concentration) and $AUC_{(0-inf)}$ (area under the plasma concentration curve from zero to infinity).

SUMMARY OF THE INVENTION

The present invention provides an immediate release aqueous solution of guaifenesin and at least one additional drug for oral administration. The solution comprises as solvents water and a total of from 48% to 72% by weight, relative to the total weight of the solution, of propylene glycol and glycerol. Further, when orally administered to an adult human subject as a single dose in an amount which affords 200 mg of guaifenesin, the solution provides (i) a $C_{max}$ of at least 3600 ng/mL of guaifenesin and/or an $AUC_{(0-inf)}$ of guaifenesin of at least 3700 ng·hr/mL and (ii) a therapeutically effective plasma concentration of guaifenesin for at least 4 hours.

In one aspect thereof, the solution may comprise, based on the total weight of the solution, a total of from 54% to 66% by weight, or from 57% to 63% by weight of propylene glycol and glycerol. For example, the solution may comprise from 15% to 23% by weight, e.g., from 17% to 21% by weight of propylene glycol and/or from 33% to 49% by weight, e.g., from 37% to 45% by weight of glycerol. Also by way of example, the weight ratio of glycerol to propylene glycol may range from 1.7:1 to 2.5:1, e.g., from 1.8:1 to 2.3:1.

In yet another aspect, the solution of the present invention may provide a $C_{max}$ of at least 3800 ng/mL of guaifenesin, e.g., at least 4000 ng/mL of guaifenesin and/or may provide an $AUC_{(0-inf)}$ of guaifenesin of at least 3900 ng·hr/mL, e.g., at least 4100 ng·hr/mL.

In another aspect, the solution may contain from 30 mg/mL to 60 mg/mL, e.g., about 40 mg/mL of guaifenesin.

In a still further aspect of the solution of the present invention, the at least one additional drug may comprise an antitussive. For example, the at least one antitussive may comprise hydrocodone and/or a pharmaceutically acceptable salt thereof such as, e.g., hydrocodone bitartrate. If any form of hydrocodone is present in the solution, the solution may comprise, for example, from 1.1 mg to 1.4 mg of hydrocodone bitartrate or an equivalent amount of hydrocodone and/or a different pharmaceutically acceptable salt of hydrocodone per 100 mg of guaifenesin contained in the solution.

In another aspect, the solution may comprise, either as an alternative or in addition to hydrocodone and/or a pharmaceutically acceptable salt thereof, one or more further drugs which are different from an antitussive, such as, e.g. at least one decongestant and/or at least one antihistamine and/or at least one analgesic. For example, the solution may comprise a decongestant such as pseudoephedrine, phenylephedrine, or a pharmaceutically acceptable salt thereof and/or may comprise one or more of brompheniramine, chlorcyclizine, chlorpheniramine, dexbrompheniramine, dexchlorpheniramine, diphenhydramine, doxylamine, phenindamine, pheniramine, pyrilamine, thonzylamine, triprolidine, and/or a pharmaceutically acceptable salt of any of these drugs.

In another aspect, the solution may further comprise a buffer such as, e.g., a citrate buffer.

The present invention also provides an immediate release solution of guaifenesin and at least one additional drug for oral administration. The solution comprises as solvents water and additionally propylene glycol and glycerol in an concentration which, when orally administered to an adult human subject as a single dose in an amount which affords 200 mg of guaifenesin, provides (i) a $C_{max}$ of guaifenesin in which is higher than the $C_{max}$ of guaifenesin provided by an otherwise identical solution without propylene glycol and glycerol by a factor of at least 1.5 and/or an $AUC_{(0-inf)}$ and/or $AUC_{(0-t)}$ of guaifenesin which is higher than the $AUC_{(0-inf)}$ and/or $AUC_{(0-t)}$ of guaifenesin provided by the aqueous solution by a factor of at least 1.4 and (ii) a therapeutically effective plasma concentration of guaifenesin (and preferably also the at least one additional drug) for at least 4 hours.

In one aspect, the solution may provide a $C_{max}$ of guaifenesin which is higher than the $C_{max}$ of guaifenesin provided by the aqueous solution by a factor of at least 1.6, e.g., by a factor of at least 1.7, or by a factor of at least 1.8 and/or may provide an $AUC_{(0-inf)}$ and/or $AUC_{(0-t)}$ of guaifenesin which is higher than the $AUC_{(0-inf)}$ and/or $AUC_{(0-t)}$ of guaifenesin provided by the aqueous solution by a factor of at least 1.5, e.g., by a factor of at least 1.6. For example, the solution may provide a $C_{max}$ of at least 3600 ng/mL of guaifenesin, e.g., at least 4000 ng/mL of guaifenesin and/or may provide an $AUC_{(0-inf)}$ and/or $AUC_{0-t}$ of guaifenesin of at least 3700 ng·hr/mL, e.g., at least 3900 ng·hr/mL. In one embodiment of the instant solution, $C_{max}$, $AUC_{inf}$ and $AUC_{0-t}$ are approximately proportional to dosage strength.

In another aspect thereof, the solution may comprise, based on the total weight of the solution, a total of from 48% to 72% by weight, e.g., from 54% to 66% by weight, or from 57% to 63% by weight of propylene glycol and glycerol. For example, the solution may comprise from 15% to 23% by weight, e.g., from 17% to 21% by weight of propylene glycol and/or from 33% to 49% by weight, e.g., from 37% to 45% by weight of glycerol and/or the weight ratio of glycerol to propylene glycol may range from 1.7:1 to 2.5:1.

In yet another aspect, the solution may contain from 30 mg/mL to 60 mg/mL of guaifenesin.

In a still further aspect of the above solution, the at least one additional drug may comprise an antitussive. For example, the at least one antitussive may comprise hydrocodone and/or a pharmaceutically acceptable salt thereof such as, e.g., hydrocodone bitartrate. If any form of hydrocodone is present in the solution, the solution may comprise, for example, from 1.1 mg to 1.4 mg of hydrocodone bitartrate or an equivalent amount of hydrocodone and/or a different pharmaceutically acceptable salt of hydrocodone per 100 mg of guaifenesin contained in the solution.

The present invention also provides a method of increasing the bioavailability of guaifenesin in an aqueous solution for oral administration, wherein the method comprises including in the solution propylene glycol and glycerol in an amount which increases the $C_{max}$ of guaifenesin by a factor of at least 1.5 and/or increases the $AUC_{(0-inf)}$ of guaifenesin by a factor of at least 1.4 when the solution is orally administered to an adult human subject as a single dose in an amount which affords 200 mg of guaifenesin.

In one aspect of the method, propylene glycol and glycerol may be included in an amount which affords a total concentration thereof of from 48% to 72% by weight, e.g., from 54% to 66% by weight, or from 57% to 63% by weight, based on the total weight of the composition. For example, the concentration of propylene glycol may be from 15% to 23% by weight, e.g., from 17% to 21% by weight of and/or the concentration of glycerol may be from 33% to 49% by weight, e.g., from 37% to 45% by weight and/or the weight ratio of glycerol to propylene glycol may range from 1.7:1 to 2.5:1.

The present invention also provides a method of alleviating a condition which can be alleviated by administration of guaifenesin and the at least one additional drug. The method comprises administering the oral solution of the present invention as set forth above, including the various aspects thereof, to a subject in need thereof.

As set forth above, the immediate release aqueous solution of guaifenesin and at least one additional drug for oral administration according to the present invention comprises concentrations of propylene glycol and glycerol which significantly increase the bioavailability of guaifenesin in the human body when compared to a solution which differs from the aqueous solution of the present invention only in that propylene glycol and glycerol are replaced by water. The concentration of water in the aqueous solution of the present invention usually is 27% to about 51% by weight, based on the total weight of the composition.

The total concentration of propylene glycol and glycerol in the aqueous solution of the present invention usually is at least 48% by weight, e.g., at least 51% by weight, at least 54% by weight, at least 57% by weight, or at least 59% by weight, but usually not higher than 72% by weight, not higher than 66% by weight, not higher than 63% by weight, or not higher than 62% by weight.

The weight ratio of glycerol to propylene glycol in the aqueous solution of the present invention usually is at least 1.7:1, e.g., at least 1.9:1, or at least 2:1, but usually not higher than 2.5:1, e.g., not higher than 2.3:1, or not higher than 2.2:1.

When orally administered to an adult human subject as a single dose in an amount which affords 200 mg of guaifenesin (e.g., 5 mL of solution containing 40 mg/mL of guaifenesin), the oral solution of the present invention usually provides a therapeutically effective plasma concentration of guaifenesin (and preferably also the at least one additional drug), i.e., a plasma concentration of guaifenesin (and the additional drug) for which a therapeutic effect can be observed, for at least 4 hours, e.g., for at least 4.5 hours, or for at least 5 hours. In addition, the solution usually provides one or both (usually both) of (a) a $C_{max}$ of guaifenesin of at least 3600 ng/mL, e.g., at least 3800 ng/mL, at least 4000 ng/mL, at least 4200 ng/mL, at least 4400 ng/mL, or at least 4500 ng/mL (and usually not higher than 6000 ng/mL, e.g., not higher than 5800 ng/mL) and (b) an $AUC_{(0-inf)}$ and/or an $AUC_{(0-t)}$ of guaifenesin of at least 3700 ng·hr/mL, e.g., at least 3900 ng·hr/mL, at least 4100 ng·hr/mL, at least 4300 ng·hr/mL, or at least 4500 ng·hr/mL (but usually not higher than 5600 ng·hr/mL, e.g, not higher than 5400 ng·hr/mL). In this regard, it is to be noted that the values for $C_{max}$, $AUC_{(0-inf)}$ and $AUC_{(0-t)}$ indicated herein are average values of plasma concentration results obtained from at least 25 adult human subjects.

Additionally or alternatively, the solution of the present invention, when orally administered to an adult human subject as a single dose in an amount which affords 200 mg of guaifenesin, provides one or both (e.g., both) of (a) a $C_{max}$ of guaifenesin which is higher than the $C_{max}$ of guaifenesin provided by an otherwise identical solution without propylene glycol and glycerol (i.e., propylene glycol and glycerol replaced by an equal amount of water) by a factor of at least 1.5, e.g., by a factor of at at least 1.6, by a factor of at at least 1.7, or by a factor of at at least 1.8, and (b) an $AUC_{(0-inf)}$ (and/or $AUC_{(0-t)}$) of guaifenesin which is higher than the $AUC_{(0-inf)}$ (and/or $AUC_{(0-t)}$) of guaifenesin provided by the aqueous solution by a factor of at least 1.4, e.g., by a factor of at least 1.5, or by a factor of at least 1.6.

As set forth above, the at least one additional drug may comprise an antitussive, such as, but not limited to, hydrocodone and/or a pharmaceutically acceptable salt thereof such as, e.g., hydrocodone bitartrate. If any form of hydrocodone is present in the solution, the solution may comprise, for example, from 1.1 mg to 1.4 mg of hydrocodone bitartrate or an equivalent amount of hydrocodone and/or a different pharmaceutically acceptable salt of hydrocodone per 100 mg of guaifenesin contained in the solution. Other antitussives which may be present in addition to or instead of hydrocodone include one or more of morphine derivatives such as one or more of codeine, dihydrocodeine, hydrocodone and hydromorphone, dextromethorphan, carbetapentane, chlophedianol, benzonatate, caramiphen, noscapine and/or one or more pharmaceutically acceptable salts of one or more of these antitussive drugs.

The term "pharmaceutically acceptable salt" as used herein and in the appended claims refers to those salts of a particular drug that are not substantially toxic at the dosage administered to achieve the desired effect and whose counterions do not independently possess significant pharmacological activity. The salts included within the scope of this term are pharmaceutically acceptable acid addition salts of a suitable inorganic or organic acid. Non-limiting examples of suitable inorganic acids include, for example, hydrochloric, hydrobromic, sulfuric and phosphoric acids. Non-limiting examples of suitable organic acids include carboxylic acids, such as acetic, propionic, tannic, glycolic, lactic, pyruvic, malonic, succinic, fumaric, malic, tartaric, citric, cyclamic, ascorbic, maleic, hydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acids, as well as sulfonic acids, such as methanesulfonic, ethanesulfonic, and β-hydroxyethanesulfonic acids.

The solution of the present invention further may comprise, either as an alternative or in addition to an antitussive such as hydrocodone and/or a pharmaceutically acceptable salt thereof, one or more further drugs which are different from an antitussive, such as, e.g. at least one decongestant and/or at least one antihistamine and/or at least one analgesic. For example, the solution may comprise one or more decongestants such as pseudoephedrine, phenylephedrine, or a pharmaceutically acceptable salt thereof and/or may comprise one or more antihistamines such as brompheniramine, chlorcyclizine, chlorpheniramine, dexbrompheniramine, dexchlorpheniramine, diphenhydramine, doxylamine, phenindamine, pheniramine, pyrilamine, thonzylamine, triprolidine, and/or a pharmaceutically acceptable salt of any of these drugs and/or may comprise one or more analgesics such as aspirin, acetaminophen, ibuprofen, ketoprofen, naproxen, sodium naproxen, meloxicam, hydrocodone, oxycodone, morphine, meperidine, fentanyl.

If desired, the solution of the present invention may also contain minor amounts of nontoxic auxiliary substances such as pH buffering agents (e.g. a citrate buffer), preservatives such as, e.g., potassium sorbate, e.g., antioxidants, solubilizing agents, flavoring agents, coloring agents, and the like.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

Example 1

For the in vivo study portions, the following general procedures were used for sample analysis unless otherwise indicated. Blood samples (3 mLs with EDTA K2 as anticoagulant) were taken prior to dosing and at specific intervals after dosing (typically between 10 minutes and 24 hours). All blood samples were chilled and centrifuged within 30 minutes of being drawn. The plasma was separated, transferred to a polypropylene tube, frozen at −20° C. and stored frozen until being shipped for drug analysis. The plasma samples were analyzed by a fully validated HPLC method. This resulting plasma concentration versus time data was subjected to pharmacokinetic analysis.

When necessary, volunteers were then given at least a seven day washout period (where no guaifenesin was administered to them under the study) prior to being crossed-over to the next treatment group.

Formulation A According to the Invention

| Raw Material | Amount per 5 mL dose | % w/w |
|---|---|---|
| CITRIC ACID USP ANHYD | 35.55 mg | 0.625 |
| GLYCERIN USP | 2333.50 mg | 41.047 |
| GUAIFENESIN USP | 200.0 mg | 3.518 |
| HYDROCODONE BITARTRATE USP | 2.5 mg | 0.044 |
| METHYLPARABEN NF | 2.050 mg | 0.036 |
| POTASSIUM CITRATE USP | 76.10 mg | 1.339 |
| POTASSIUM SORBATE POWDER NF | 8.100 mg | 0.142 |
| PROPYLENE GLYCOL USP | 1080.00 mg | 18.997 |
| PROPYLPARABEN NF | 0.700 mg | 0.012 |
| PURIFIED WATER USP | 1,922.972 mg | 33.826 |
| RASPBERRY FLAVOR ART. | 5.528 mg | 0.097 |
| SACCHARIN SODIUM USP | 18.00 mg | 0.317 |
| | 5685 mg/5 mL | |

The in vivo behavior of the above formulation was compared to the corresponding behavior of co-administered (a) commercially available hydrocodone bitartrate and homatropine methylbromide syrup (Formulation B) and (b) guaifenesin dissolved in water (Formulation C), all at the same concentration of guaifenesin and with the same amount of formulation. The open label study involved 35 healthy adult human subjects. The results of the pharmacokinetic parameters analysis are set forth in Table 1 below.

| Commercial Hydrocodone Bitartrate and Homatropine Syrup (Formulation B) | |
|---|---|
| Raw Material | Amount per 5 mL dose |
| HYDROCODONE BITARTRATE USP | 5 mg |
| HOMATROPINE METHYLBROMEDE USP | 1.5 mg |
| CARMEL COLOR | Not Available |
| CHERRY FLAVOR | Not Available |
| CITRIC ACID | Not Available |
| FD&C RED #40 | Not Available |
| METHYLPARABEN | Not Available |
| PROPYLPARABEN | Not Available |
| PURIFIED WATER | Not Available |
| SORBITOL SOLUTION | Not Available |
| SUCROSE SYRUP | Not Available |
| SODIUM CITRATE TO pH | Not Available |

TABLE 1

| Parameter | Formulation A | Formulation B + Formulation C | Formulation C | Ratio A/C | Ratio (B + C)/C |
|---|---|---|---|---|---|
| $AUC_{(0-t)}$ | 4610 | 2979 | 2834 | 1.627 | 1.051 |
| $AUC_{(0-inf)}$ | 4641 | 3014 | 2869 | 1.618 | 1.051 |
| $C_{max}$ | 4577 | 2878 | 2420 | 1.891 | 1.189 |
| Ln-transformed | | | | | |
| $AUC_{(0-t)}$ | 4200 | 2778 | 2602 | 1.614 | 1.068 |
| $AUC_{(0-inf)}$ | 4243 | 2817 | 2643 | 1.606 | 1.066 |
| $C_{max}$ | 4029 | 2629 | 2205 | 1.828 | 1.193 |

As can be seen from the above results, the rate of absorption of guaifenesin from the formulation of the present invention (Formulation A), as assessed by $C_{max}$ and $AUC_{(0-inf)}$ and $AUC_{(0-t)}$, is not bioequivalent to the guaifenesin aqueous solution (Formulation C). Additionally, the rate of absorption of guaifenesin from Formulation A, as assessed by $C_{max}$ and $AUC_{(0-inf)}$ and $AUC_{(0-t)}$, also is not bioequivalent to the co-administration of hydrocodone bitartrate and homatropine methylbromide syrup plus guaifenesin aqueous solution (Formulation B+Formulation C).

In conclusion, the rate of guaifenesin absorption from the formulation according to the present invention is significantly enhanced compared to both Formulation C and Formulation B+Formulation C, apparently due to the presence of glycerol and propylene glycol in Formulation A (i.e., not due to the presence of hydrocodone bitartrate in Formulation A, as evidenced by the nearly identical results for Formulation B+Formulation C and Formulation C).

The following Examples provide additional oral guaifenesin solutions according to the present invention.

Example 2

| Raw Material | Amount per 5 mL dose | % W/W |
|---|---|---|
| CITRIC ACID USP ANHYD | 35.55 mg | 0.625 |
| GLYCERIN USP | 2333.50 mg | 41.047 |
| GUAIFENESIN USP | 200.0 mg | 3.518 |
| HYDROCODONE BITARTRATE USP | 2.5 mg | 0.044 |
| METHYLPARABEN NF | 2.050 mg | 0.036 |
| PSEUDOEPHEDRINE HCl | 30.00 mg | 0.528 |
| POTASSIUM CITRATE USP | 76.10 mg | 1.339 |
| POTASSIUM SORBATE POWDER NF | 8.100 mg | 0.142 |
| PROPYLENE GLYCOL USP | 1080.00 mg | 18.997 |
| PROPYLPARABEN NF | 0.700 mg | 0.012 |
| PURIFIED WATER USP | 1,892.972 mg | 33.298 |
| RASPBERRY FLAVOR ART. | 5.528 mg | 0.097 |
| SACCHARIN SODIUM USP | 18.00 mg | 0.317 |
| | 5685 mg/5 mL | |

Example 3

| Raw Material | Amount per 5 mL dose | % W/W |
|---|---|---|
| CITRIC ACID USP ANHYD | 35.55 mg | 0.625 |
| GLYCERIN USP | 2333.50 mg | 41.047 |
| CHLORPHENIRAMINE MALEATE | 2.0 mg | 0.035 |
| GUAIFENESIN USP | 200.0 mg | 3.518 |
| HYDROCODONE BETARTRATE USP | 2.5 mg | 0.044 |
| METHYLPARABEN NF | 2.050 mg | 0.036 |
| POTASSIUM CITRATE USP | 76.10 mg | 1.339 |
| POTASSIUM SORBATE POWDER N F | 8.100 mg | 0.142 |
| PROPYLENE GLYCOL USP | 1080.00 mg | 18.997 |
| PROPYLPARABEN NF | 0.700 mg | 0.012 |
| PURIFIED WATER USP | 1,920.972 mg | 33.791 |
| RASPBERRY FLAVOR ART. | 5.528 mg | 0.097 |
| SACCHARIN SODIUM USP | 18.00 mg | 0.317 |
| | 5685 mg/5 mL | |

Example 4

| Raw Material | Amount per 5 mL dose | % W/W |
|---|---|---|
| CITRIC ACID USP ANHYD | 35.55 mg | 0.625 |
| GLYCERIN USP | 2333.50 mg | 41.047 |
| CHLORPHENIRAMINE MALEATE | 2.0 mg | 0.035 |
| GUAEFENESIN USP | 200.0 mg | 3.518 |
| HYDROCODONE BETARTRATE USP | 2.5 mg | 0.044 |
| PSUEDOEPHEDRINE HCl | 30.000 mg | 0.528 |
| METHYLPARABEN NF | 2.050 mg | 0.036 |
| POTASSIUM CITRATE USP | 76.10 mg | 1.339 |
| POTASSIUM SORBATE POWDER NF | 8.100 mg | 0.142 |
| PROPYLENE GLYCOL USP | 1080.00 mg | 18.997 |
| PROPYLPARABEN NF | 0.700 mg | 0.012 |
| PURIFIED WATER USP | 1,890.972 mg | 33.263 |
| RASPBERRY FLAVOR ART. | 5.528 mg | 0.097 |
| SACCHARIN SODIUM USP | 18.00 mg | 0.317 |
| | 5685 mg/5 mL | |

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. An immediate release solution for oral administration of guaifenesin and one or more additional drugs, wherein the one or more additional drugs comprise at least one of an antitussive, a decongestant, an antihistamine or an analgesic and the solution comprises as solvents water and a total of from 48% to 72% by weight, relative to a total weight of the solution, of propylene glycol and glycerol, and wherein the solution, when orally administered to an adult human subject as a single dose in an amount which affords 200 mg of guaifenesin, provides (i) a $C_{max}$ of at least 3600 ng/mL of guaifenesin and/or an $AUC_{(0\text{-}inf)}$ of guaifenesin of at least 3700 ng·hr/mL and (ii) a therapeutically effective plasma concentration of guaifenesin for at least 4 hours.

2. The solution of claim 1, wherein the solution comprises a total of from 54% to 66% by weight of propylene glycol and glycerol.

3. The solution of claim 1, wherein a weight ratio of glycerol to propylene glycol is from 1.7:1 to 2.5:1.

4. The solution of claim 1, wherein the solution comprises from 15% to 23% by of propylene glycol.

5. The solution of claim 1, wherein the solution comprises from 33% to 49% by weight of glycerol.

6. The solution of claim 1, wherein the solution provides a $C_{max}$ of at least 3800 ng/mL of guaifenesin.

7. The solution of claim 1, wherein the solution provides a $C_{max}$ of at least 4000 ng/mL of guaifenesin.

8. The solution of claim 6, wherein the solution provides an $AUC_{(0\text{-}inf)}$ of guaifenesin of at least 3900 ng·hr/mL.

9. The solution of claim 7, wherein the solution further provides an $AUC_{(0\text{-}inf)}$ of guaifenesin of at least 4100 ng·hr/mL.

10. The solution of claim 1, wherein the one or more additional drugs comprise a decongestant.

11. The solution of claim 10, wherein the decongestant comprises at least one of pseudoephedrine and a pharmaceutically acceptable salt thereof.

12. The solution of claim 10, wherein the decongestant comprises at least one of phenylephrine and a pharmaceutically acceptable salt thereof.

13. The solution of claim 1, wherein the one or ore additional drugs comprise an antihistamine.

14. The solution of claim 13, wherein the antihistamine comprises at least one of brompheniramine, chlorcyclizine, chlorpheniramine, dexbrompheniramine, dexchlorpheniramine, diphenhydramine, doxylamine, phenindamine, pheniramine, pyrilamine, thonzylamine, triprolidine, and/or a pharmaceutically acceptable salt of any of these drugs.

15. The solution of claim 1, wherein the one or more additional drugs comprise an analgesic.

16. An immediate release solution for oral administration of guaifenesin and one or more additional drugs, wherein the one or more additional drugs comprise at least one of an antitussive, a decongestant, an antihistamine or an analgesic and the solution comprises as solvents water and additionally propylene glycol and glycerol in a concentration which, when orally administered to an adult human subject as a single dose in an amount which affords 200 mg of guaifenesin, provides in (i) a $C_{max}$ of guaifenesin which is higher than the $C_{max}$ of guaifenesin provided by an aqueous solution without propylene glycol and glycerol that comprises the same concentrations of guaifenesin and the at least one additional drug by a factor of at least 1.5 and/or an $AUC_{(0-inf)}$ of guaifenesin which is higher than the $AUC_{(0-inf)}$ of guaifenesin provided by the aqueous solution by a factor of at least 1.4 and (ii) a therapeutically effective plasma concentration of guaifenesin for at least 4 hours.

17. The solution of claim 16, wherein the solution provides a $C_{max}$ of guaifenesin which is higher than the $C_{max}$ of guaifenesin provided by an aqueous solution by a factor of at least 1.6 and an $AUC_{(0-inf)}$ of guaifenesin which is higher than the $AUC_{(0-inf)}$ of guaifenesin provided by the aqueous solution by a factor of at least 1.5.

18. The solution of claim 17, wherein the solution comprises a total of from 48% to 72% by weight of propylene glycol and glycerol, based on a total weight of the solution.

19. The solution of claim 16, wherein the one or more additional drugs comprise a decongestant.

20. The solution of claim 16, wherein the one or more additional drugs comprise an antihistamine.

* * * * *